(12) United States Patent
Prusiner

(10) Patent No.: US 7,163,806 B2
(45) Date of Patent: Jan. 16, 2007

(54) SOMATIC CELLS WITH ABLATED PRP GENE AND METHODS OF USE

(75) Inventor: Stanley B. Prusiner, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 527 days.

(21) Appl. No.: 10/773,795

(22) Filed: Feb. 6, 2004

(65) Prior Publication Data

US 2004/0141959 A1 Jul. 22, 2004

Related U.S. Application Data

(63) Continuation of application No. 09/829,507, filed on Apr. 9, 2001, now Pat. No. 6,797,495, which is a continuation of application No. 09/220,265, filed on Dec. 22, 1998, now abandoned, which is a continuation-in-part of application No. 08/740,947, filed on Nov. 5, 1996, now Pat. No. 5,834,593.

(51) Int. Cl.
*C12N 15/00* (2006.01)
*A61K 48/00* (2006.01)
*A01K 67/00* (2006.01)

(52) U.S. Cl. ...................... 435/69.7; 514/44; 424/93.1; 800/8

(58) Field of Classification Search ................ None
See application file for complete search history.

(56) References Cited

U.S. PATENT DOCUMENTS

| | | | |
|---|---|---|---|
| 5,182,366 A | 1/1993 | Huebner et al. | |
| 5,387,746 A | 2/1995 | Whitsett | |
| 5,420,246 A | 5/1995 | Rutter et al. | |
| 5,552,381 A | 9/1996 | Atkinson | |
| 5,565,186 A | 10/1996 | Prusiner et al. | |
| 5,605,691 A | 2/1997 | Carroll | |

FOREIGN PATENT DOCUMENTS

| | | |
|---|---|---|
| WO | WO 93/10277 | 5/1993 |
| WO | WO 00/26238 | 5/2000 |

OTHER PUBLICATIONS

Oancea AE, et al. J Immunol Dec. 15, 1995; 155 (12):5678-83.*
Wettey FR, et al. Science Aug. 30, 2002; 297: 1521-1525.*
Robakis et al., "Isolation of a cDNA clone encoding the leader peptide of prion protein and expression of the homologous gene in various tissues" *Proc. Natl. Acad. Sci. USA*, 83:6377-6381 (Sep. 1986).
Brown et al., "Prion protein-deficient cells show altered response to oxidative stress due to decreased SOD-1 activity," *Experimental Neurology* 146:104-112 (1997).
Büeler, H., et al "Normal development of mice lacking the neuronal cell-surface PrP protein" *Nature* 356, 577-582 (1992).
Capecchi, M.R., "Site directed mutagenesis by gene targeting in mouse embryo derived stem cells," *Cell* 51:503-512 (1987).
B.W. Caughey, et al., "Secondary structure analysis of the scrapie-associated protein PrP 27-30 in water by infrared spectroscopy," *Biochemistry* 30, 7672-7680 (1991).
B. Caughey, et al., "Aggregates of scrapie-associated prion protein induce the cell-free conversion of protease-sensitive prion protein to the protease-resistant state," *J. Chem. Biol.* 2, 807-817 (1995).
Chazot, et al., "New variant of Creuzfeldt-Jacob disease in a 26-year old French man," *Lancet* 347:1181 (1996).
F.E. Cohen, et al., "Structural clues to prion replication," *Science* 264:530-531 (1994).
M. Fischer, et al., "Prion protein (PrP) with amino-proximal deletions restoring susceptibility of PrP knockout mice to scrapie," *EMBO J.* 15:1255-64.
R. Gabizon, et al., "Properties of scrapie prion protein liposomes," *J. Biol. Chem.* 263:4950-4955 (1988).
Gabriel et al., "Molecular cloning of a candidate chicken prion protein," *Proc. Natl. Acad. Sci. USA* 89:9097-9101 (1992).
M. Gasset, et al., "Predicted α-helical regions of the prion protein when synthesized as peptides from amyloid," *Proc. Natl. Acad. Sci. USA* 89:10940-10944 (1992).
M. Gasset, et al., "Perturbation of the secondary structure of the scrapie prion protein under conditions that alter infectivity," *Proc. Natl. Acad. Sci. USA* 90:1-5 (1993).
D.A. Kocisko, et al., "Cell-free formation of protease-resistant prion protein," *Nature* 370, 471-474 (1994).
Harlow et al., *Antibodies: A Laboratory Manual*, Cold Spring Harbor Laboratory pp. 148-155 (1988).
J.W. Herms et al., "Patch clamp analysis of synaptic transmission to cerebellar Purinje cells of prion protein knockout mice," *Eur. J. Neuroscience* 7:2508-2512 (1995) (Abstract).
Z. Huang, et al., "Proposed three-dimensional structure for the cellular prion protein," *Proc. Natl. Acad. Sci. USA* 91:7139-7143 (1994).
Z. Huang, et al., "Scrapie prions: a three-dimensional model of an infectious fragment," *Folding & Design* 1:13-19 (1996).
C. Locht, et al., "Molecular cloning and complete sequence of prion protein cDNA from mouse brian infected with the scrapie agent," *Proc. Natl. Acad. Sci. USA* 83:6372-6276 (1986).
I. Mehlhorn, et al., "High-level expression and characterization of a purified 152-residue polypeptide of the prion protein," *Biochemistry* 35:5528-5537 (1996).
R.K. Meyer, et al., "Separation and properties of cellular and scrapie prion proteins," *Proc. Natl. Acad. Sci. USA* 83:2310-2314 (1986).

(Continued)

Primary Examiner—Bruce R. Campell
Assistant Examiner—Michelle Horning
(74) Attorney, Agent, or Firm—Karl Bozicevic; Bozicevic, Field & Francis LLP

(57) ABSTRACT

The present invention comprises a method for producing mammalian therapeutics free from prion contamination and cells for use in such methods. Such therapeutics are produced in somatic cells having a genome with an artificially altered PrP gene. The PrP gene in these cells may be ablated, or replaced by an exogenous inducible form of the PrP gene. The endogenous gene in the host cells may be disrupted, or disrupted and replaced by an exogenous PrP gene.

10 Claims, No Drawings

OTHER PUBLICATIONS

J. Nguyen, et al., "Prion protein peptides induce α-helix to β-sheet conformational transitions," *Biochemistry* 34:4186-4192 (1995).

K.M. Pan, et al., "Conversion of α-helices into β-sheets features in the formation of the scrapie prion proteins," *Proc. Natl. Acad. Sci. USA* 90:10962-10966 (1993).

S.B. Prusiner, et al., "Further purification and characterization of scrapie-prions," *Biochemistry* 21:6942-6950 (1982).

S.B. Prusiner, et al., "Scrapie prions aggregate to form amyloid-like birefringent rods," *Cell* 35:349-358 (1983).

S.B. Prusiner, et al., "Purification and structural studies of a major scrapie prion protein," *Cell* 38:127-134 (1984).

S.B. Prusiner et al., *Science* vol. 252, pp. 1515-1522 (Jun. 14, 1991).

S.B. Prusiner, et al., "Ablation of the prion protein (PrP) gene in mice prevents scrapie and facilitates production of anti-PrP antibodies," *Proc. Natl. Acad. Sci. USA* 90:10608-10612 (1993).

R. Riek, et al., "NMR structure of the mouse prion protein domain PrP(121-231)," *Nature* 382:180-182 (1996).

M. Rogers, et al., "Epitope mapping of the syrian hamster prion protein utilizing chimeric and mutant genes in a vaccinia virus expression system," *J. Immunol.* 147:3568-3574 (1991).

M. Rogers, et al., "Conversion of truncated and elongated prion proteins into the scrapie isoform in cultured cells," *Proc. Natl. Acad. Sci. USA* 90:3182-3186 (1993).

Sauer et al., *Proc. Natl. Acad. Sci. USA*, 85:5166-5170 (Jul. 1988).

Sauer et al., *The New Biologist*, vol. 2, 441-449 (May 1990).

J. Safar, et al., "Conformational transitions, dissociation, and unfolding of scrapie amyloid (prion) protein," *J. Biol. Chem.* 268:20276-20284 (1993).

M. Scott, et al., "Prion protein gene expression in cultured cells," *Protein Engineering* 2:69-76 (1988).

M.R. Scott, et al., "Chimeric prion protein expression in cultured cells and transgenic mice," *Protein Sci.* 1:986-997 (1992).

Shigematsu et al., *J. Biol Chem* 267(30):21329-37 (Oct. 25, 1992).

N. Stahl, et al., "Scrapie prion protein contains a phosphatidylinositol glycolipid," *Cell* 51:229-240 (1987).

Strandberg et al., *Appl. Environ. Microbiol.* 57(6):1669-74 (Jun. 1991).

Tagliavini et al., *Biochemical & Biophysical Research Communications* vol. 184, pp. 1398-1404 (May 15, 1992).

A. Taraboulos, et al., "Acquisition of protease resistance by prion proteins in scrapie-infected cells does not require asparagine-linked glycosylation," *Proc. Natl. Acad. Sci. USA* 87:8262-6.

A. Taraboulos, et al., "Cholesterol depletion and modification of COOH-terminal targeting sequence of the prion protein inhibit formation of the scrapie isoform," *J. Cell Biol.* 129:121-132 (1995).

E. Turk, et al., "Purification and properties of the cellular and scrapie hamster prion proteins," *Eur. J. Biochem.* 176:21-30 (1988).

R.G. Will, et al., "New variant of Creuzfeldt-Jacob disease in the UK," *Lancet* 347, 921-925 (1996).

R.A. Williamson, et al., "Circumventing tolerance to generate autologous monoclonal antibodies to the prion protein," *Proc. Natl. Acad. Sci. USA* 93:7279-7282 (1996).

C.S. Yost, et al., "Non-hydrophobic extracytoplasmic determinant of stop transfer in the prion protein," *Nature* 343:669-672 (1990).

Zhang et al., *J. Biol. Chem.* 269(45):27799-27802 (Nov. 11, 1994).

H. Zhang, et al., "Conformational transitions in peptides containing two putative α-helices of the prion protein," *J. Mol. Biol.* 250:514-526 (1995).

* cited by examiner

SEQUENCE LISTING

<160> NUMBER OF SEQ ID NOS: 3

<210> SEQ ID NO 1
<211> LENGTH: 34
<212> TYPE: DNA
<213> ORGANISM: Homo sapiens

<400> SEQUENCE: 1
ataacttcgt ataatgtatg ctatacgaag ttat        34

<210> SEQ ID NO 2
<211> LENGTH: 34
<212> TYPE: DNA
<213> ORGANISM: Homo sapiens

<400> SEQUENCE: 2
acaacttcgt ataatgtatg ctatacgaag ttat        34

<210> SEQ ID NO 3
<211> LENGTH: 34
<212> TYPE: DNA
<213> ORGANISM: Homo sapiens

<400> SEQUENCE: 3
ataacttcgt ataatgtata ctatacgaag ttat        34

US 7,163,806 B2

SOMATIC CELLS WITH ABLATED PRP GENE AND METHODS OF USE

CROSS-REFERENCE

This application is a continuation of application Ser. No. 09/829,507, filed Apr. 9, 2001, now U.S. Pat. No. 6,797,495 which is a continuation of application Ser. No. 09/220,265, filed Dec. 22, 1998 now abandoned, which application is a continuation in part application of Ser. No. 08/740,947, filed Nov. 5, 1996 (now U.S. Pat. No. 5,834,593 issued Nov. 10, 1998) all of which are incorporated herein by reference in their entirety and to which applications we claim priority under 35 USC § 120.

GOVERNMENT RIGHTS

The United States Government may have certain rights in this application pursuant to Grant No. AG10770 awarded by the National Institutes of Health.

FIELD OF THE INVENTION

The invention relates generally to the field of somatic cells and cell lines altered with respect to the expression of a gene detrimental to early development, and particularly relates to cells with an altered PrP gene.

BACKGROUND OF THE INVENTION

Prions are infectious pathogens that cause central nervous system spongiform encephalopathies in animals. Prions are distinct from bacteria, viruses and viroids. The predominant hypothesis at present is that no nucleic acid component is necessary for infectivity of prion protein. Further, a prion which infects one species of animal (e.g., a human) will not infect another (e.g., a mouse).

A major step in the study of prions and the diseases that they cause was the discovery and purification of a protein designated prion protein ("PrP") [Bolton et al., *Science* 218:1309–11 (1982); Prusiner et al., *Biochemistry* 21:6942–50 (1982); McKinley et al., *Cell* 35:57–62 (1983)]. Complete prion protein-encoding genes have since been cloned, sequenced and expressed in transgenic animals. $PrP^C$ is encoded by a single-copy host gene [Basler et al., *Cell* 46:417–28 (1986)] and is normally found at the outer surface of neurons. A leading hypothesis is that prion diseases result from conversion of $PrP^C$ into a modified form called $PrP^{Sc}$.

At present, it appears that the scrapie isoform of the prion protein ($PrP^{Sc}$) is necessary for both the transmission and pathogenesis of the transmissible neurodegenerative diseases of animals and humans. See Prusiner, S. B., "Molecular biology of prion disease," *Science* 252:1515–1522 (1991). The most common prion diseases of animals are scrapie of sheep and goats and bovine spongiform encephalopathy (BSE) of cattle [Wilesmith, J. and Wells, *Microbiol. Immunol.* 172:21–38 (1991)]. Four prion diseases of humans have been identified: (1) kuru, (2) Creutzfeldt-Jakob Disease (CJD), (3) Gerstmann-Strassler-Scheinker Disease (GSS), and (4) fatal familial insomnia (FFI) [Gajdusek, D. C., *Science* 197:943–960 (1977); Medori et al., *N. Engl. J. Med.* 326:444–449 (1992)]. The presentation of human prion diseases as sporadic, genetic and infectious illnesses initially posed a conundrum which has been explained by the cellular genetic origin of PrP.

Some cases of human prion disease have been transmitted to rodents but apparently with less regularity than transmission between animals of the same species [Gibbs, Jr. et al., *Slow Transmissible Diseases of the Nervous System*, Vol. 2, S. B. Prusiner and W. J. Hadlow,. eds. (New York: Academic Press), pp. 87–110 (1979); Tateishi et al., *Prion Diseases of Humans and Animals*, Prusiner et al., eds. (London: Ellis Horwood), pp. 129–134 (1992)]. The infrequent transmission of human prion disease to rodents has been cited as an example of the "species barrier" first described by Pattison in his studies of passaging the scrapie agent between sheep and rodents [Pattison, I. H., *NINDB Monograph* 2, D. C. Gajdusek, C. J. Gibbs Jr. and M. P. Alpers, eds. (Washington, D.C.: U.S. Government Printing), pp. 249–257 (1965)]. In those investigations, the initial passage of prions from one species to another was associated with a prolonged incubation time with only a few animals developing illness. Subsequent passage in the same species was characterized by all the animals becoming ill after greatly shortened incubation times.

The molecular basis for the species barrier between Syrian hamster (SHa) and mouse was shown to reside in the sequence of the PrP gene using transgenic (Tg) mice [Scott et al., *Cell* 59:847–857 (1989)]. SHaPrP differs from MoPrP at 16 positions out of 254 amino acid residues [Basler et al., *Cell* 46:417–428 (1986); Locht et al., *Proc. Natl. Acad. Sci. USA* 83:6372–6376 (1986)]. Tg(SHaPrP) mice expressing SHaPrP had abbreviated incubation times when inoculated with SHa prions. When similar studies were performed with mice expressing the human, or ovine PrP transgenes, the species barrier was not abrogated, i.e., the percentage of animals which became infected were unacceptably low and the incubation times were unacceptably long. Thus, it has not been possible, for example in the case of human prions, to use transgenic animals (such as mice containing a PrP gene of another species) to reliably test a sample to determine if that sample is infected with prions. Such a test was first disclosed in application Ser. No. 08/242,188 filed May 13, 1994 which is now U.S. Pat. No. 5,565,186 issued Oct. 15, 1996.

Most human CJD cases are sporadic, but about 10–15% are inherited as autosomal dominant disorders that are caused by mutations in the human PrP gene [Hsiao et al., *Neurology* 40:1820–1827 (1990); Goldfarb et al., *Science* 258:806–808 (1992); Kitamoto et al., *Proc. R. Soc. Lond.* 343:391–398 (1994)]. Iatrogenic CJD has been caused by human growth hormone derived from cadaveric pituitaries as well as dura mater grafts [Brown et al., *Lancet* 340:24–27 (1992)]. Despite numerous attempts to link CJD to an infectious source such as the consumption of scrapie infected sheep meat, none has been identified to date [Harries-Jones et al., *J. Neurol. Neurosurg. Psychiatry* 51:1113–1119 (1988)] except in cases of iatrogenically induced disease. On the other hand, kuru, which for many decades devastated the Fore and neighboring tribes of the New Guinea highlands, is believed to have been spread by infection during ritualistic cannibalism [Alpers, M. P., *Slow Transmissible Diseases of the Nervous System*, Vol. 1, S. B. Prusiner and W. J. Hadlow, eds. (New York: Academic Press), pp.66–90 (1979)].

More than 45 young adults previously treated with HGH derived from human pituitaries have developed CJD [Koch et al., *N. Engl. J. Med.* 313:731–733 (1985); Brown et al., *Lancet* 340:24–27 (1992); Fradkin et al., *JAMA* 265:880–884 (1991); Buchanan et al., *Br. Med. J.* 302:824–828 (1991)]. Fortunately, recombinant HGH is now used, although the seemingly remote possibility has been raised that increased expression of wt $PrP^C$ stimulated by high HGH might induce prion disease [Lasmezas et al., *Biochem. Biophys. Res. Commun.* 196:1163–1169 (1993)]. That the HGH prepared from pituitaries was contaminated with prions is supported by the transmission of prion disease to a monkey 66 months after inoculation with a suspect lot of HGH [Gibbs, Jr. et al., *N. Engl. J. Med.* 328:358–359 (1993)]. The long incubation times associated with prion diseases will not reveal the full extent of iatrogenic CJD in thousands of people treated with HGH worldwide. Iatrogenic CJD also appears to have developed in four infertile women treated with contaminated human pituitary-derived gonadotrophin hormone [Healy et al., *Br. J. Med.* 307: 517–518 (1993); Cochius et al., *Aust. N.Z. J. Med.* 20:592–593 (1990); Cochius et al., *J. Neurol. Neurosurg. Psychiatry* 55:1094–1095 (1992)] as well as at least 11 patients receiving dura mater grafts [Nisbet et al., *J. Am. Med. Assoc.* 261:1118 (1989); Thadani et al., *J. Neurosurg.* 69:766–769 (1988); Willison et al., *J. Neurosurg. Psychiatric* 54:940 (1991); Brown et al., *Lancet* 340:24–27 (1992)]. These cases of iatrogenic CJD underscore the need for screening pharmaceuticals that might possibly be contaminated with prions.

Two doctors in France were charged with involuntary manslaughter of a child who had been treated with growth hormones extracted from corpses. The child developed Creutzfeldt-Jakob Disease. (See *New Scientist*, Jul. 31, 1993, page 4). According to the Pasteur Institute, since 1989 there have been 24 reported cases of CJD in young people who were treated with human growth hormone between 1983 and mid-1985. Fifteen of these children have died. It now appears as though hundreds of children in France have been treated with growth hormone extracted from dead bodies at the risk of developing CJD (see *New Scientist*, Nov. 20, 1993, page. 10.) In view of such, there clearly is a need for a convenient, cost-effective method for producing human products such as growth hormone that are free from any potentially contagious prion contamination.

The risk of transmitting prion-related disorders through therapeutic human products is a serious health concern. One method for preventing the transmission of prion related disorders is to produce recombinant human products in organisms such as *Escherichia coli* and *Saccharomyces cerevisiae*, since these organisms do not have an endogenous PrP gene and thus are not susceptible to $PrP^{Sc}$ infection While *Escherichia coli* and *Saccharomyces cerevisiae* production is ideal for the large scale synthesis of many human proteins, factors such as plasmid stability and insolubility of the desired protein product may limit the usefulness of these systems in some circumstances. In addition, certain recombinantly-produced proteins require post-translational modification to obtain the function of the endogenous protein, and thus may require synthesis in mammalian cells or even species-specific cell lines for proper functioning of the produced protein. For example, a recombinant human thryotropin (rhTSH) produced in Chinese Hamster Ovary cells is more highly sialylated than a nonrecombinant, cadaver-derived pituitary hTSH. The rhTSH also has a 2-fold lower metabolic clearance rate than pituitary TSH, resulting in a greater than 10-fold higher serum concentration of rhTSH compared to pituitary hTSH. (Thotakura et al., *Endocrinology* 128:341–348 (1991)) Since it is desirable to use therapeutic agents with the proper post-translational modifications, mammalian systems are preferable for the production of such proteins.

Moreover, other therapeutic agents, such as antibodies, are exclusively produced by mammalian cell systems. Classical cell fusion techniques allow efficient production of monoclonal antibodies by fusing the B cell producing the antibody with an immortalized mammalian cell line. The resulting cell line is called a hybridoma cell line. Applications of human antibodies produced by these hybridoma systems have promising potential in the area of cancer, immunodeficiencies, and other diseases involving an immune response. For instance, the apoptosis-inducing human monoclonal antibody SC-1 has been shown to cause a significant induction of apoptotic activity in eight patients with poorly differentiated stomach adenocarcinoma (Vollmers et al. *Oncol Rep* 5:549–552 (1998)). In another example, the antibody to HER2/neu has been shown to be a promising therapy for human breast cancer (Valero, (1998) *Semin. Oncol.* 5: 549–552). Monoclonal antibodies produced in murine hybridoma systems require an additional step of "humanizing" the antibodies to prevent the antibodies from being recognized as foreign epitopes (See e.g. Sato et al., (1994) Mol. Immunol. 31: 371–381). These systems are susceptible to prion infection, and antibodies produced in infected cells pose a risk of transmission to any individual receiving antibodies from the infected sources.

Since many therapeutics are produced in mammalian systems, there is a need for ensuring the safety of the products isolated from such systems. Given the potential for the transmission of disease when these therapeutics are extracted from tissue, there is a need for a method of producing therapeutics that are free from the risk of human disease-causing contaminants such as prions.

SUMMARY OF THE INVENTION

A method for producing mammalian therapeutics free from prion contamination, cells for use in such methods, and prion-free therapeutic formulations produced via the cells are disclosed. The invention comprises producing such therapeutics in somatic cells having a genome with an artificially altered PrP gene. The PrP gene in these cells may be ablated, or replaced by an exogenous inducible form of the PrP gene. Preferably, the cells of the invention are from mouse, rat, hamster, cow, sheep, horse, pig, dog, cat, chicken, more preferably from primates, and most preferably human. These cells may be derived from transgenic animals with an altered PrP gene, or the PrP may have been altered in the cell. Such cells are no longer susceptible to PrP infection ($PrP^{Sc}$), as infection requires an interaction between the infectious prion agent and the endogenous form of the protein ($PrP^C$). Therapeutics produced by such a method include, but are not limited to, peptides, proteins, antibodies, antisense RNA molecules, ribozymes, viral vectors, and the like. Any of the therapeutics can be combined with a carrier to provide an appropriate pharmaceutical formulation which is prion free.

The invention features cells and a method of producing therapeutics using somatic mammalian cells in which the endogenous PrP gene has been disrupted and an exogenous PrP gene has been introduced into the genome. The endogenous PrP gene may be disrupted and the exogenous PrP later introduced into the cells, or the endogenous PrP gene may be disrupted by replacement of the,endogenous PrP gene with the exogenous form of the PrP gene, e.g. by site-specific homologous recombination. In addition, the introduced PrP gene may or may not be integrated into the cell's genome.

In one embodiment, the invention features the production of therapeutics in host cells expressing exogenous PrP sequences from a species genetically diverse from the host cells. These cells express PrP$^C$, but are protected from prion infection from the host cell species-specific PrP$^{Sc}$.

In another embodiment, the invention features the production of therapeutics in host cells expressing exogenous PrP sequences of the same species as the host cell, with the endogenous form of PrP ablated.

Another aspect of the invention is a method of producing antibodies in a hybridoma cell with a disrupted endogenous PrP gene. The disruption of the PrP gene may follow the fusion of the antibody-producing B-cell with the immortalized cell line, and may occur either prior to the establishment of the hybridoma as a cell line or following establishment. Alternatively, the prion-free hybridoma cell line may be produced by transfecting B cells from animals with a disrupted, PrP gene, thereby ablating the endogenous PrP gene of the B cell. These transfected B cells can be fused with an immortalized cell line which also has an ablated PrP gene, resulting in a hybridoma with no endogenous PrP expression that is resistant to prion infection.

Another aspect of the invention is the adaption of monoclonal antibodies for use of therapeutics by alteration and subsequent production in mammalian cells which cells have a disrupted endogenous PrP. Again, the endogenous PrP gene may be ablated or replaced with an inducible form of the PrP gene. Preferably, the therapeutic produced is a human antibody, and the antibody is "humanized" in a PrP knock-out primate cell line.

An object of the invention is to provide a method for producing biological products that are free from the risk of prion infection, and thus will not transmit prion-related disorders to subjects receiving such products.

Another object of the invention is to provide a method for ensuring both bioactivity and safety of mammalian therapeutics.

A feature of the invention is that the cells used in the invention are not susceptible to prion infection.

An advantage of the invention is that the method ensures that biologic products created by this method are prion free.

An object is to provide a range of therapeutics and formulations thereof which are prion-free.

These and other objects, advantages, and features of the invention will become apparent to those persons skilled in the art upon reading the details of the invention as more fully described below.

DETAILED DESCRIPTION OF PREFERRED EMBODIMENTS

Before the present cell lines, methods and prion-free products are described, it is to be understood that this invention is not limited to particular cell lines, methods, or products described and may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "an," and "the" include plural referents unless the context clearly dictates otherwise. Thus, for example, reference to "a construct" includes a plurality of such constructs and reference to "a mammalian cell" includes reference to one or more mammalian cells, cell lines and equivalents thereof known to those skilled in the art, and so forth.

All publications mentioned herein are incorporated herein by reference for the purpose of describing and disclosing, for example, the cell lines, constructs, and methodologies that are described in the publications which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention. Further, the publication dates provided may be different from the actual publication date which may require independent verification.

DEFINITIONS

The term "isolated" shall mean separated away from its natural environment. An isolated protein is not necessarily separated away from all materials it is normally present with and may remain glycosylated.

The terms "therapeutic" or "therapeutic agent" as used herein generally mean any chemical or biological molecule used to obtain a desired pharmacologic, biologic, physiologic and/or psychologic effect. The effect may be prophylactic in terms of completely or partially preventing a disease or symptom thereof and/or may be therapeutic in terms of a partial or complete cure for a disease and/or adverse effect attributable to the disease. Therapeutics as used herein covers any compound used in the treatment of a disease in a mammal, particularly a human, and includes compositions for:

(a) preventing a disease or symptom from occurring in a subject which may be predisposed to the disease or symptom but has not yet been diagnosed as having it;

(b) inhibiting a disease symptom, i.e., arresting its development; or (c) relieving a disease symptom, i.e., causing regression of the disease.

The term "treatment" is used herein to mean administering a "therapeutic" to obtain all or any of the desired results of a "therapeutic."

A "knock-out" or "ablation" of a gene, which terms are used interchangeably herein, means an alteration in the sequence of the gene or sequence associated with the gene that results in a decrease of function of the target gene, preferably such that target gene expression is undetectable or insignificant. An ablation of an endogenous PrP gene means that the function of any endogenous PrP gene has been substantially decreased so that expression is not detectable or only present at insignificant levels. "Knock-out" transgenics can be transgenic animals having a heterozygous knock-out of the PrP gene (PrP$^{+/0}$) or a homozygous knock-out of the PrP gene (PrP$^{0/0}$). "Knock-outs" also include conditional knock-outs, where alteration of the target gene can occur upon, for example, exposure of the animal to a substance that promotes target gene alteration, introduction of an enzyme that promotes recombination at the target gene site (e.g., Cre in the Cre-lox system), or other method for directing the target gene alteration postnatally.

The term "Prnp-$^{0/0}$" or "Prnp-Abl" refers to a transgenic animal which has its PrP gene ablated with the "$^{0/0}$" indicating that both alleles are ablated whereas $^{o/+}$ indicates only one is ablated. Specifically, the animal being referred to is generally a transgenic mouse which has its PrP gene ablated i.e., a PrP knock-out mouse. In that the PrP gene is disrupted no mouse PrP protein is expressed.

The term "prion" shall mean an infectious particle known to cause diseases (spongiform encephalopathies) in humans and animals. The term "prion" is a contraction of the words "protein" and "infection" and the particles are comprised largely if not exclusively of PrP$^{Sc}$ molecules encoded by a PrP gene which expresses PrP$^C$ which changes conformation to become PrP$^{Sc}$. Prions are distinct from bacteria, viruses and viroids. Known prions include those which infect animals to cause scrapie, a transmissible, degenerative disease of the nervous system of sheep and goats as well as bovine spongiform encephalopathies (BSE) or mad cow disease and feline spongiform encephalopathies of cats. Four prion diseases known to affect humans are (1) kuru, (2) Creutzfeldt-Jakob Disease (CJD), (3) Gerstmann-Strassler-Scheinker Disease (GSS), and (4) fatal familial insomnia (FFI). As used herein prion includes all forms of prions causing all or any of these diseases or others in any animals used—and in particular in humans and in domesticated farm animals. Prions include all infectious variants of the PrP$^{Sc}$ protein.

The terms "PrP gene" and "prion protein gene" are used interchangeably herein to describe genetic material which expresses PrP proteins. The term "PrP gene" refers generally to any gene of any species which encodes any form of a PrP amino acid sequence including any prion protein. Some commonly known PrP sequences are described in Gabriel et al., *Proc. Natl. Acad. Sci. USA* 89:9097–9101 (1992) which is incorporated herein by reference to disclose and describe such sequences.

The terms "standardized prion preparation," "prion preparation," "preparation" and the like are used interchangeably herein to describe composition containing prions which composition is obtained from brain tissue of mammals which contain substantially the same genetic material as relates to PrP proteins, e.g., brain tissue from a set of mammals which exhibit signs of prion disease which mammals may comprise any of (1) a PrP chimeric transgene; (2) an ablated endogenous PrP gene; (3) a high; copy number of PrP genes from a genetically diverse species; or (4) hybrids with an ablated endogenous PrP gene and a PrP gene from a genetically diverse species. The mammals from which standardized prion preparations are obtained exhibit clinical signs of CNS dysfunction as a result of inoculation with prions and/or due to their genetically modified make up, e.g., high copy number of PrP genes.

The terms "ablated PrP protein gene," "disrupted PrP gene," "ablated PrP gene," "PrP$^{0/0}$" and the like are used interchangeably herein to mean an endogenous PrP gene which has been altered (e.g., add and/or remove nucleotides) in a manner so as to render the gene inoperative. Examples of nonfunctional PrP genes and methods of making such are disclosed in Büeler, H., et al. "Normal development of mice lacking the neuronal cell-surface PrP protein," *Nature* 356: 577–582 (1992) which is incorporated herein by reference. Both alleles of the genes are disrupted.

The terms "resistant to infection", "resistant to infection with prions" and the like mean the cells include an altered PrP gene which renders the cells resistant to prion disease when inoculated with an amount and type of prion which would be expected to cause prion disease should the exposed cells or a product of the exposed cells be introduced in an animal of the same species.

The term "prion-free" means the composition contains an insufficient amount of prions (PrP$^{Sc}$) to cause an infection and preferably contains no detectable amount of prions using current detection technology and most preferably contains no prion at all.

The terms "susceptible to infection" and "susceptible to infection by prions" and the like are used interchangeably herein to describe cells which can be infected by prions, such infected cells being able to cause a subject animal to develop a disease if inoculated with these infected cells or products produced in such cells.

The term "incubation time" shall mean the time from inoculation of an animal with a prion until the time when the animal first develops detectable symptoms of disease resulting from the infection. A reduced incubation time is six months or less, preferably about 75 days ±25 days or less, more preferably about 30 days ±10 days or less.

The terms "genetically diverse animal" and "genetically diverse mammal" are used to describe an animal which includes a native PrP codon sequence which differs from the genetically diverse test animal by 17 or more codons, preferably 20 or more codons, and most preferably 28–40 codons from the host cell. Thus, a mouse PrP gene is genetically diverse with respect to the PrP gene of a human, cow or sheep, but is not genetically diverse with respect to the PrP gene of a hamster.

The term "antibody" stands for an immunoglobulin protein which is capable of binding an antigen. Antibody as used herein is meant to include the entire antibody as well as any antibody fragments (e.g. F(ab', Fab, Fv) capable of binding the epitope, antigen or antigenic fragment of interest. Preferred antibodies for assays of the invention are immunoreactive or immunospecific for and therefore specifically and selectively bind to a PrP protein. Antibodies which are immunoreactive and immunospecific for both native PrP$^C$ and treated PrP$^{Sc}$ but not native PrP$^{Sc}$ are preferred. Antibodies for PrP are preferably immunospecific—e.g., not substantially cross-reactive with related materials. The term "antibody" encompasses all types of antibodies, e.g. polyclonal, monoclonal, and those produced by the phage display methodology. Particularly preferred antibodies of the invention are antibodies which have a relatively high degree of affinity for the target antigen.

"Purified antibody" refers to that which is sufficiently free of other proteins, carbohydrates, and lipids with which it is naturally associated. Such an antibody "preferentially binds" to a treated or denatured PrP$^{Sc}$ protein (or an antigenic fragment thereof), and does not substantially recognize or bind to other antigenetically unrelated molecules. A purified antibody of the invention is preferably immunoreactive with and immunospecific for a specific species.

"Antigenic fragment" of a protein (e.g., HER2/neu) means a portion of such a protein which is capable of binding an antibody.

By "binds specifically" is meant high avidity and/or high affinity binding of an antibody to a specific polypeptide e.g., epitope of a protein such as a HER2/neu protein. Antibody binding to the epitope on this specific polypeptide is preferably stronger than binding of the same antibody to any other epitope, particularly those which may be present in molecules in association with, or in the same sample, as the specific polypeptide of interest e.g., binds more strongly to epitope fragments of a protein such as HER2/neu so that by adjusting binding conditions the antibody binds almost exclusively to an epitope site or fragments of a desired protein such as an epitope fragment exposed by treatment of HER2/neu and not exposed on related receptors of the same subfamily.

Cells with a Disrupted PrP Gene

Preferably, the product of the PrP gene in cells used in the method of the invention is undetectable, insignificant, and most preferably non-existent. A knock-out of an endogenous PrP gene means that the function of the PrP protein has been substantially decreased so that PrP protein expression is not detectable or only present at insignificant levels. This may be achieved by a variety of mechanisms, including introduction of a disruption of the coding sequence, e.g. insertion of one or more stop codons, insertion of a DNA fragment, deletion of coding sequence, substitution of stop codons for coding sequence, etc. In some cases the exogenous transgene sequences are ultimately deleted from the genome, leaving a net change to the native sequence. Different approaches may be used to achieve the "knock-out." See U.S. Pat. Nos. 5,464,764, 5,627,059 and related patents and publications to Capecchi et al. A chromosomal deletion of all or part of the native gene may be induced, including deletions of the non-coding regions, particularly the promoter region, 3' regulatory sequences, enhancers, or deletions of gene that activate expression of PrP genes. A functional knock-out may also be achieved by the introduction of an anti-sense construct that blocks expression of the native genes (for example, see Li and Cohen (1996) *Cell* 85:319–329). "Knock-outs" also include conditional knock-outs, for example where alteration of the target gene occurs upon exposure of the animal to a substance that promotes target gene alteration, introduction of an enzyme that promotes recombination at the target gene site (e.g. Cre in the Cre-lox system), or other methods for directing the target gene alteration.

In general, site-specific recombination-facilitating sequences useful in the present invention encompass any nucleotide sequence that facilitates site-specific recombination by interaction of a specific enzyme with two such site-specific recombination-facilitating sequences. Exemplary site-specific recombination facilitating sequences include, but are not necessarily limited to: PNS vectors as described in U.S. Pat. No. 5,627,059; lox sequences (recombination mediated by Cre enzyme); frt sequences (Golic et al. (1989) *Cell* 59:499–509 and O'Gorman et al. (1991) *Science* 251:1351–5); recombination mediated by the FLP recombinase; the recognition sequences for the pSR1 recombinase of *Zygosaccharomyces rouxii* (Matsuzaki et al. (1990) *J. Bacteriol.* 172:610–8); and the like. Each of these can be used to alter endogenous PrP expression by disrupting the endogenous gene, i.e. creating a PrP knock-out, and/or by replacing the endogenous gene with an inducible form of PrP, i.e. creating a conditional PrP knock-out.

The exogenous introduced PrP gene may be a mammalian PrP gene which is operably linked to an inducible promoter. By "operably linked" is meant that a DNA sequence and a regulatory sequence(s) are connected in such a way as to permit gene expression when the appropriate molecules, e.g. transcriptional activator proteins, are bound to the regulatory sequence(s). Such an inducible PrP gene functions as a conditional knock-out, since induction of PrP can be reversibly controlled.

Specific constructs of interest include, but are not limited to, anti-sense PrP, which will block native PrP expression, expression of dominant negative PrP mutations, and over-expression of a PrP gene. A detectable marker, such as lac Z may be introduced into the locus, where upregulation of expression will result in an easily detected change in phenotype. Constructs utilizing the PrP promoter region, in combination with a reporter gene or with the coding region, are also of interest.

DNA constructs for homologous recombination will comprise at least a portion of the PrP gene with the desired genetic modification, and will include regions of homology to the target locus. DNA constructs for random integration need not include regions of homology to mediate recombination. Conveniently, markers for positive and negative selection are included. Methods for generating cells having targeted gene modifications through homologous recombination are known in the art. For various techniques for transfecting mammalian cells, see Keown et al. (1990) *Methods in Enzymology* 185:527–537.

PrP Nucleic Acid Compositions

The term "PrP" is used generically to designate PrP genes, e.g. homologs from rat, human, mouse, guinea pig, etc., and their alternate forms. Used generically, this term encompasses different iso forms, polymorphisms, variant sequences, and mutated forms of PrP as well. The term is also intended to mean the open reading frame encoding specific polypeptides, introns, and adjacent 5' and 3' non-coding nucleotide sequences involved in the regulation of expression, up to about 1 kb beyond the coding region, but possibly further in either direction. The DNA sequences encoding PrP may be cDNA or genomic DNA or a fragment thereof. The gene may be introduced into an appropriate vector for extrachromosomal maintenance or for integration into the host. The amino acid sequences and DNA sequences for a number of animals are known, see U.S. Pat. Nos. 5,565,186; 5,763,740; 5,789,655; 5,792,901 and publications cited in these patents for sequences, isoforms, polymorphisms, variants and mutations.

A genomic sequence of interest comprises tie nucleic acid present between the initiation codon and the stop codon, as defined in the sequences listed here and in the cited patents and publications, including all of the introns that are normally present in a native chromosome. It may further include the 3' and 5' untranslated regions found in the mature mRNA. It may further include specific transcriptional and translational regulatory sequences, such as promoters, enhancers, etc., including about 1 kb, but possibly more, of flanking genomic DNA at either the 5' or 3' end of the transcribed region. The genomic DNA may be isolated as a fragment of 100 kbp or smaller; and substantially free of flanking chromosomal sequence.

The sequence of this 5' region, and further 5' upstream sequences and 3' downstream sequences, may be utilized for promoter elements, including enhancer binding sites, that provide for expression in tissues where PrP is expressed. The tissue specific expression is useful for determining the pattern of expression, and for providing promoters that mimic the native pattern of expression. Naturally occurring polymorphisms in the promoter region are useful for determining natural variations in expression, particularly those that may be associated with disease. Alternatively, mutations may be introduced into the promoter region to determine the effect of altering expression in experimentally defined systems. Methods for the identification of specific DNA motifs involved in the binding of transcriptional factors are known in the art, e.g. sequence similarity to known binding motifs, gel retardation studies, etc. For examples, see Blackwell et al (1995) *Mol Med* 1:194–205; Mortlock et al. (1996) *Genome Res*. 6:327–33; and Joulin and Richard-Foy (1995) *Eur J Biochem* 232:620–626.

The regulatory sequences may be used to identify cis acting sequences required for transcriptional or translational regulation of PrP expression, especially in different tissues or stages of development, and to identify cis acting sequences and trans acting factors that regulate or mediate expression. Such transcription or translational control regions may be operably linked to a PrP gene in order to promote or prevent expression of wild type or altered PrP or other proteins of interest in cultured cells.

The nucleic acid compositions used in the subject invention may encode all or a part of the PrP polypeptides as appropriate. Fragments may be obtained of the DNA sequence by chemically synthesizing oligonucleotides in accordance with conventional methods, by restriction enzyme digestion, by PCR amplification, etc. For the most part, DNA fragments will be of at least 15 nt, usually at least 18 nt, more usually at least about 50 nt. Such small DNA fragments are useful as primers for PCR, hybridization screening, etc. Larger DNA fragments, i.e. greater than 100 nt are useful for production of the encoded polypeptide. For use in amplification reactions, such as PCR, a pair of primers will be used.

Techniques for in vitro mutagenesis of cloned genes are known. Examples of protocols for scanning mutations may be found in Gustin et al., 1993 Biotechniques 14:22; Barany, 1985 Gene 37:111–23; Colicelli et al., 1985 Mol Gen Genet 199:537–9; and Prentki et al., 1984 Gene 29:303–13. Methods for site specific mutagenesis can be found in Sambrook et al., 1989 Molecular Cloning: A Laboratory Manual, CSH Press, pp. 15.3–15.108; Weiner et al., 1993 Gene 126:35–41; Sayers et al., 1992 Biotechniques 13:592–6; Jones and Winistorfer, 1992 Biotechniques 12:528–30; Barton et al., 1990 Nucleic Acids Res 18:7349–55; Marotti and Tomich, 1989 Gene Anal Tech 6:67–70; and Zhu 1989 Anal Biochem 177:120–4. For example, a chicken, bovine, sheep, rat and mouse PrP gene are disclosed and published within Gabriel et al., *Proc. Natl. Acad. Sci. USA* 89:9097–9101 (1992). The sequence for the Syrian hamster is published in Basler et al., *Cell* 46:417–428 (1986). The PrP gene of sheep is published by Goldmann et al., *Proc. Natl. Acad. Sci. USA* 87:2476–2480 (1990). The PrP gene sequence for bovine is published in Goldmann et al., *J. Gen. Virol.* 72:201–204 (1991). The sequence for chicken PrP gene is published in Harris et al., *Proc. Natl. Acad. Sci. USA* 88:7664–7668 (1991). The PrP gene sequence for mink is published in Kretzschmar et al., *J. Gen. Virol.* 73:2757–2761 (1992). The human PrP gene sequence is published in Kretzschmar et al., *DNA* 5:315–324 (1986). The PrP gene sequence for mouse is published in Locht et al., *Proc. Natl. Acad. Sci. USA* 83:6372–6376 (1986). The PrP gene sequence for sheep is published in Westaway et al., *Genes Dev.* 8:959–969 (1994). These publications are all incorporated herein by reference to disclose and describe the PrP gene and PrP amino acid sequences.

Tetracycline Inducible System

The tetracycline (tet)-regulated trans-activation systems for inducible gene expression allows temporal and quantitative control of exogenous genes in mammalian cells, transgenic mice and plants. For review, see Shockett, PNAS 43:5173–5176 (1996), which is incorporated by reference herein. The pioneering tet-regulated gene expression system involved a constitutive expression of the tet transactivator protein (tTA) with the cytomegalovirus (CMV) immediate early (IE) promoter/enhancer. tTA is a fusion protein composed of the tet repressor of *Escheria coli* and the transcriptional activation domain of the VP16 protein of herpes simplex virus. In the absence of tetracycline, the tet repressor portion of tTA mediates high affinity binding to sequences from the tet resistance operator of Tn10 (tetO). In the presence of tetracycline, a conformational change in the tet repressor prevents tTA from binding to its operator.

A modified system has also been developed using a reverse transactivator (rtTA) that binds tetO efficiently only in the presence of the tet derivatives doxycycline or anhydrotetracycline. It is hypothesized that this system is especially useful in situations where cells or individuals were to be kept in the repressed state for long periods of time and where long term exposure to tet or one of its derivatives was undesirable, or in situations requiring rapid induction.

Although the preferred embodiment of the present invention feature a tetracycline-inducible system driven by the CMV promoter, other methods of delivery of the tet-regulated genes and other resistant factors may be used. For example, viral vectors driven by either the SV40 promoter, by glial-cell specific promoters, or by the autonomous parvovirus LuIII may be used to express tTA. These and other similar systems may be used in the present invention without departing from the spirit of the disclosure, as will be obvious to those skilled in the art. For example, systems such as ecdysome inducible systems can be used instead of the tetracycline inducible system.

Production of Antibodies

Antibodies are prepared in accordance with conventional methods, where the expressed polypeptide or protein is used as an immunogen, by itself or conjugated to known immunogenic carriers, e.g. KLH, pre-S HBsAg, other viral or eukaryotic proteins, or the like. Various adjuvants may be employed, with a series of injections, as appropriate. For monoclonal antibodies, after one or more booster injections, the spleen is isolated, the lymphocytes immortalized by cell fusion, and then screened for high affinity antibody binding. The immortalized cells, i.e. hybridomas, producing the desired antibodies may then be expanded. For further description, see *Monoclonal Antibodies: A Laboratory Manual*, Harlow and Lane eds., Cold Spring Harbor Laboratories, Cold Spring Harbor, N.Y., 1988.

Once a suitable monoclonal antibody has been identified as a potential therapeutic agent, the antibody must be adapted for use in the subject organism. Altering the antibody to conform to the immune system of the subject species serves two basic functions: it decreases the chance of a significant adverse reaction of the host immune response to the therapeutic antibody, and it increases the therapeutic activity of the antibody since the activity is less likely to be neutralized by the host immune system. For example, antibodies used as human therapeutics are routinely "humanized" before used to treat human ailments.

There are many approaches to humanizing monoclonal antibodies, each of which designs and constructs a reshaped human antibody which mimics the mouse antibody. For instance, one approach bases the design of the human antibody on the most homologous consensus sequence. Another approach bases the design on the most homologous human antibody. Both of these approaches utilize primate cell cultures, and therefore bear the risk of contamination with $PrP^{Sc}$ and potential infection of people treated with such therapeutics. Elimination of the endogenous PrP gene in the cell lines used to humanize these antibodies can prevent this occurrence.

EXAMPLES

The following examples are put forth so as to provide those of ordinary skill in the art with a complete disclosure and description of how to make and use the subject invention, and are not intended to limit the scope of what is regarded as the invention nor are they intended to represent or imply that the experiments shown are all or the only experiments performed. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

Example 1

Production of Human Thyrotropin

The presence and specific structure of moieties such as oligosaccharides on certain proteins has been shown to be important for both the production and bioactivity of these proteins. Since the carbohydrate structure of a protein is determined in part by the glycosylation apparatus of the cells in which the protein is produced, the type of host cell producing this protein directly influences the in vivo activity of the protein. It is thus desirable for proteins that require certain carbohydrate composition to be produced in cells containing the apparatus necessary to provide proper post-translational modification.

As cellular apparatus controlling post-translational modification varies even between cells from different mammalian species, some human proteins are preferably produced in primate cells. One group of proteins that are sensitive to such modifications are the pituitary and chorionic glycoprotein hormones. To ensure the safety of these proteins with respect to prion infectivity, these proteins can be produced in cells without a functioning human prion protein. Production of these proteins using the method of the invention is thus preferably done in suitable, prion free cells.

Preparation of a Human Neuronally-derived PrP Knock-out Cell Line

The neuroblastoma cell line N2a is one cell type that may be used in the method of the present invention to produce properly modified human proteins. The activity of the endogenous PrP gene in the N2a cell line is eliminated using the homologous recombination technology as described in U.S. Pat. No. 5,627,059. The '059 patent uses a PNS vector comprised of a four component construct: a first and second sequence homologous to sequences in the PrP gene; a positive selection DNA sequence inserted between the first and second homologous sequences; and a negative selection sequence connected on either side of the homologous sequences, but not positioned between the two. When the first and second homologous sequences undergo homologous recombination with the homologous target sequences in the PrP gene, the positive selection sequence is inserted while the negative sequence is not. Cells without the positive selection sequence did not undergo recombination at the PrP locus, and cells with the negative selection sequences have an inserted sequence in the genome, but did not undergo homologous recombination at the PrP gene. N2a cells with a disrupted PrP are thus selected by homologous recombination by the presence of the positive selection sequences and absence of the negative selection sequence.

The N2a cells with the disrupted PrP gene are selected for use for producing the human thyrotropin. Since these cells do not contain the endogenous PrP gene, they are no longer at risk of infection by the $PrP^{Sc}$ form of the protein. These N2a cells may thus be classified as a "prion free" cell line, and the products produced in this cell line may also be characterized as "prion free," meaning that products produced from such prion free cell lines do not pose a risk to individuals receiving in vivo therapy using products produced from these cell lines.

Production of Human Thyrotropin in the PrP Knock-out Cell Line

Human TSH is a member of the pituitary and chorionic glycoprotein hormones, and contains two non-covalently linked subunits, $\alpha$ and $\beta$. To produce hTSH, a complementary DNA for human choriogonadotropin a and an hTSH $\beta$ minigene, described in Wondisford et al. (1988) *Mol Endocrin* 2:32–39, are cotransfected into the prion-free N2a cells. Stable transfectants with high rates of TSH production are selected. The expressed TSH is purified from culture supernatants by chromatography on Blue-Trisacryl M (IBF Biotechnics, Savage, Md.), Q-sepharose Fast Flow and S-Sepharose Fast Flow (Both from Pharmacia, Piscataway, N.J.). Final purity of the isolated TSH is generally greater than 97%.

Example 2

Production of Protein in a Human Cell Line with Inducible PrP

Certain cell lines may be sensitive to the presence of PrP, and thus it may be desirable to have PrP expression at certain times in the cultivation of the cell line, e.g. during the establishment of the PrP knock-out cell line or for selection purposes. To this end, a cell line with no endogenous PrP but with an inducible PrP gene will allow expression of $PrP^C$ during necessary periods of cultivation of the cell line, but then will allow the cells to be prion free for the production of therapeutics. These cell lines can be produced by inserting an inducible prion transgene into the parent cell line, and then disrupting the endogenous form of the PrP gene.

Replacement of the Endogenous PrP Gene with an Inducible PrP Gene

To produce HeLa cells with the endogenous PrP gene replaced with an inducible transgene, sequences encoding lox sites are used to promote site-specific recombination. A lox site is a nucleotide sequence at which the gene product of the cre gene, referred to herein as "Cre," catalyzes site-specific recombination. A particularly preferred lox site is a loxP site. The sequence of loxP, which is 34 bp in length, is known and can be produced synthetically or can be isolated from bacteriophage P1 by methods known in the art (see, e.g., Hoess et al. (1982) *Proc. Natl. Acad. Sci. USA* 79:3398). The loxP site is composed of two 13 bp inverted repeats separated by an 8 bp spacer region. The nucleotide sequences of the insert repeats and the spacer region of loxP are as follows:
 ATAACTTCGTATA ATGTATGC TATACGAAGTTAT (SEQ ID NO:1)

Other suitable lox sites include loxB, loxL, and loxR, which can be isolated from *E. coli* (Hoess et al. (1982) *Proc.*

Natl. Acad. Sci. USA 22:3398). Preferably, the lox site used is either loxP or loxC2. The nucleotide sequences of the insert repeats and the spacer region of loxC2 are as follows:

ACAACTTCGTATA ATGTATGC TATACGAAGTTAT (SEQ ID NO:2)

The site-specific recombination-facilitating sequences useful in the present invention may be either a naturally-occurring sequence or a modified sequence. For example, PCT published application no. WO 93/19172 describes phage vectors in which the VH10 genes are flanked by two loxP sites, one of which is a mutant loxP site (loxP511), in which the G at the seventh position in the spacer region of loxP is replaced with an A, preventing recombination within the vector from merely excising the $V_H$ genes. However, two loxP511 sites can recombine via Cre-mediated recombination and, therefore, can be recombined selectively in the presence of one or more wild-type lox sites. The nucleotide sequences of the insert repeats and the spacer region of loxP511 are as follows:

ATAACTTCGTATA ATGTATAC TATACGAAGTTAT (SEQ ID NO:3)

Lox sites can also be produced by a variety of synthetic techniques which are known in the art. For example, synthetic techniques for producing lox sites are disclosed by Ogilvie et al. (1981) Science, 21A: 270.

The lox target is placed into the genome of cultured HeLa cells using methods known in the art. The lox-neo target is placed into the HeLa cells by electroporating $10^7$ cells in 0.8 ml with 1 µg of a site specific integration vector, pSF1, containing loxP sequences and an unmodified neo gene sequence (Fukushige (1992) PNAS 89: 7905–7909). Electroporation uses a single pulse of 450 V at 500 µF from a BioRad Gene Pulser™. One day later, cells are selected for growth in an $\alpha^-$ medium which lacks deoxyribonucleosides and ribonucleosides supplemented with 15% dialyzed fetal bovine serum.

Cre-mediated integration of the lox targeting vectors used the same electroporation conditions with 10 µg of targeting vector and 20 µg of the target constructs. Target constructs containing the HuPrP open reading frame are obtained by cloning a promoterless genomic fragment downstream from the heptamerized tetracycline operator in the pUHD10-3 vector to obtain tetO-HuPrP. The tetO-HuPrP fragment is then cloned into vector pBS226 behind the hCMV promoter. Each electroporated sample is plated into a 10-cm culture dish. Two days later cells were selected for growth in medium with G418 (400 µg/ml). Colony formation was scored 12 days later and individual clones were selected for expansion. The antibiotics doxycycline or minocycline are both potent repressors of the tTA-dependent LacZ activity, and either added to a concentration of 1 µg/ml at the time of transfection repress the $PrP^C$ levels. Cell lines with stable formation of HuPrP are selected using techniques well known to those in the art.

To produce prion free proteins in the PrP inducible cell lines, the cells should be grown for a determined number of passages free from tetracycline to ensure there is no detectable PrP expression in these cells. Complementary DNA for a human protean may then be transfected into the HeLa cells, and stable transfectants selected. The protein of interest may be isolated from these cells by any number of methods commonly used by those skilled in the art.

Example 3

Production of HER-2/NEU Antibodies in Prion Resistant Hybridomas

To produce antibodies in cells resistant to prion infection, the endogenous mouse PrP gene can be disrupted in the hybridoma line. The endogenous PrP gene is preferably disrupted following fusion, but may take place either prior to or after establishment of the hybridoma cell lines. The endogenous PrP gene is disrupted using a vector based on adeno-associated virus (AAV) that can efficiently modify homologous human chromosomal target sequences. The protocol used is elucidated in Russel and Hirata (1998) Nat. Genet 18: 325–330, which is incorporated herein by reference. The vector contains sequences homologous to the mouse PrP gene sufficient for proper homologous recombination, but the sequences do not encode a functional PrP gene.

Immunization of Mice with HER-2/NEU Antigen

Six female BALB/c mice are immunized intraperitoneally for the initial production of antibody. For each mouse, the injection solution contains 250 µl of complete Freund's adjuvant mixed with 250 µl prepared HER-2/NEU antigen solution. The injection may contain between 1 and 200 µg of the antigen, and the antigen may or may not be covalently linked to a small immunogenic hapten or a large immunogenic protein such as a hemocyanin. After two weeks, each animal is given a boost dose of a similar amount, but using 250 µl incomplete Freund's as the adjuvant.

At day 24, tail bleeds are collected from the mice to test for immunogenic response to the antigen. The bleeds are diluted 1:5 in PBS, and samples from each mouse are compared with similar dilutions of a non-inmmunized control mouse in an assay to determine immune response, such as a dot blot assay. On day 35, each animal is injected with 250 µl incomplete Freund's, and at day 45 tail bleeds are again taken and serum samples screened by immunoprecipitation against in vivo radiolabeled HER-2/NEU antigen preparation. The animals with serum responding strongly to the antigen are injected at day 56 with 100 µl antigen solution intravenously and 100 µl antigen solution intraperitoneally. At day 59, the splenocytes from the strong responders are fused with a BALB/c myeloma cell line.

Fusion of Myeloma and Splenocytes to Create Hybridoma

The prion resistant hybridoma lines that produce the HER-2/NEU antibodies are created following the fusion of the splenocytes producing the HER-2/NEU antibodies with the myeloma cell line. The fusion may be effected by any fusogen known to those skilled in the art, and preferably polyethylene glycol. The myeloma cells used in the fusion process carry a mutation in the hypoxanthine-guanine phosphoribosyl transferase gene (HPRT), and thus immortalized cells that have undergone fusion with the splenocytes are selected by the addition of any compound that blocks the de novo nucleotide synthesis pathway, such as methotrexate or aminopterin. Fused cells that survive such a screen are expanded.

Ablation of the PrP Gene in the HER-2/NEU Hybridoma Lines

The endogenous gene or genes of the hybridoma cell line may be disrupted using a construct encoding a green fluorescent binding protein (GFP) under the control of a mammalian promoter or enhancer, preferably CMV-IE. GFP is a reporter gene that does not require any substrate for detection, and may be used as a marker for the transgenic cells. The construct carrying the GFP transgene may be as illustrated in Takada, et al., "Selective Production of Transgenic Mice Using Green Fluorescent Protein as a Marker," *Nature Biotechnology* (1997) 15:458–461, which is incorporated herein by reference. The disruption of the endogenous PrP gene using such a method may allow an easy identification of candidate cell populations in which the homologous recombination event has occurred, and the selection may be confirmed using more traditional methods such as Southern blot analysis.

The activity of the endogenous PrP gene in the selected hybridomas expressing the HER-2/NEU monoclonal antibodies can be ablated using the homologous recombination technology as described in U.S. Pat. No. 5,627,059 and above in Example 1. The hybridoma cells with the disrupted PrP gene are selected using a fluorescent microscope. The hybridoma cells expressing the GFP can be clonally expanded, and then the clonal population can be screened for the presence of endogenous $PrP^C$. Hybridoma cells-with no remaining PrP sequences expressed can be classified as "prion free", and the antibodies produced therefrom should pose no risk of infection.

Example 4

Humanization of Monoclonal Antibodies to HER-2/NEU

The cDNA coding for the mouse monoclonal antibody that recognizes HER-2/neu (hereafter "ANTI-NEU") is modified by PCR to have EcoRI and Kozak sequences at the 5' end and HindIII sites and splice donor sequences at the 3' end (see eg. Maeda et al. (1991) *Hum. Antibod. Hybridomas* 2:124–134; Kettleborough et al., (1991) *Protein Engng* 4:773–783). The V regions are then linked to the genes encoding human constant regions under the control of the human elongation factor 1-α promoter-enhancer region (HEF), with $V_L$ linked to human kappa constant region and $V_H$ linked to the gamma-1 constant region.

The gene coding for the reshaped ANTI-NEU $V_L$ region is constructed by PCR-based CDR-grafting method as illustrated in Sato, et al., "Humanization of a Mouse Anti-Human Interleukin-6 Receptor Antibody Comparing Two Methods for Selecting Human Framework Regions," *Mol. Immunol.* (1994) 31:371–381 which is incorporated herein by reference. Eight PCR primers are designed. The external primers A and H hybridize to DNA sequences in the pUC19 vector into which the cDNA encoding the humanized ANTI-NEU antibody is cloned, and each encodes a different endonuclease restriction site for cloning purposes. The CDR-grafting primers B, C, D have the DNA sequences coding for CDR1, CDR2, and CDR3, respectively, of mouse ANTI-NEU variable regions. The complementary primers E, F and G consist of 15–20 bases which are the complementary DNA sequences on the 5'-side of primers B, C and D, respectively. In the first PCR step, four reactions, reactions A-E, B-F, C-G and D-H, are carried out using human light chain sequences cloned into pUC19 as a template. In a second step, the four PCR products from the first PCR step are assembled by their own complementarity. External primers are then added to the reaction, and the full-length DNA product is amplified. The final PCR product is digested with the appropriate restriction endonucleases, and cloned into a pUC19 vector. After the PCR product is sequenced for verification, it is cloned into the HEF expression vector.

The gene coding for the reshaped ANTI-NEU $V_H$ region is also constructed using the CDR grafting method described above, using a consensus amino acid sequence for human $V_H$ regions belonging to subgroup I (HSG-I). This sequence is also cloned into the HER expression vector.

The activity of the endogenous $PrP^C$ gene in the COS cell line is eliminated using the homologous recombination technology as described in Example 1. COS cells with a disrupted PrP gene are thus selected for the disruption of the PrP gene by homologous recombination by the presence of the positive selection sequences and absence of the negative selection sequence. The COS cells with the disrupted PrP gene are then used to produce the humanized antibodies. Since these cells do not contain the endogenous PrP gene, they are no longer at risk of infection by the $PrP^{Sc}$ form of the protein. These COS cells are thus classified as a "prion free" cell line, and the products produced in this cell line may also be characterized as "prion free," meaning that products produced from such prion free cell lines do not pose a risk to individuals receiving in vivo therapy using products produced from these cell lines.

The light and heavy chain expression vectors are co-transfected into the COS-PrP knock-out line by electroporation. Equal amounts of each plasmid DNA (10 μg) are added to 0.8 ml of cells suspended in PBS at $1\times10^7$ ml$^{-1}$. A pulse is delivered at 1.9 kV, 25 μF capacitance using a Gene Pulsar™ apparatus (BioRad). After a 10 minute recovery period at room temperature, the electroporated cells are added to 20 ml DMEM containing 10% gamma globulin-free fetal calf serum (GIBCO™). After a 2 hour incubation, the medium is collected, centrifuged to remove cellular debris, and applied to a Protein A agarose column (Affi-Gel Protein A MAPSII™ kit, BioRad) equilibrated with binding buffer. The elute is concentrated, and the buffer changed to PBS using a microconcentrator.

Example 5

Production of Monoclonal Antibodies to SC-1

The hybridoma cell lines may be found to grow more efficiently with limited PrP expression, and to this end it may be desirable to have modulated PrP expression in the hybridoma cells. This can be accomplished by replacing the endogenous PrP gene found in the hybridoma cells with a transgene containing an inducible $PrP^C$ protein that can be suppressed for production of the antibodies. The endogenous hybridoma PrP-encoding sequences are replaced using site-specific insertion of a transgene encoding an inducible $PrP^C$ protein. The approach involves gene targeting to introduce an FRT site into the genomic region containing the endogenous PrP sequences to create a "transgene acceptor site," followed by a single-copy insertion of transgene into the targeted FRT site using FRT recombinase (see, e.g. Wigley et al. *Reprod. Fertil. Dev.*, which is incorporated herein by reference).

A cassette is made to insert the inducible PrP gene into the hybridoma genome and inserted into the PrP locus of the hybridoma cells. This cassette contains a fully functional neomycin resistance gene flanked by direct repeats of the FRT site. The neo gene will act as a positive selection marker, and targeting events can be monitored by Southern blot analysis to ensure that no endogenous PrP sequences remain. Once this is accomplished, the hybridoma cells will be transfected with a source of FLP recombinase to excise the neo gene. This will generate a single FRT site at a single PrP locus, and the loss of neo sequences may be monitored by Southern analysis. FLP recombinase is used to insert a single copy of the inducible PrP gene into the newly created FRT site. This involves a co-transfection of a plasmid containing a source of FLP and a plasmid containing the inducible PrP sequences linked to a single FRT.

Example 6

Humanization of Monoclonal Antibodies to SC-1

The gene coding for the reshaped SC-1 $V_L$ region is constructed using the CDR-grafting protocol of Example 4, and closed into a HER expression vector.

The heavy chain region is designed based on the amino acid sequence of the human HAX $V_H$ region, as described in Dersimoninan et al. (1987) *J. Immun.* 139:2496–2501, which is incorporated herein in its entirety. First, the mouse SC-1 $V_H$ sequence is compared to the human HAX $V_H$ sequence, and a human SC-1 $V_H$ is designed to mimic the structure of the mouse antibody. The designed human $V_H$ DNA sequence is divided into 6 overlapping oligonucleotide sequences of approximately 90–94 base pairs in length, with an approximate overlap of 20 base pairs. Three of the oligonucleotides have sense DNA sequence, and the other three have antisense DNA sequence. Two external primers are also designed. The six oligonucleotides are assembled and the full length DNA amplified with the external primers. The PCR product is digested with EcoRI and HindIII, and subcloned into a pUC19 vector. Each oligonucleotide is analyzed by computer for possible secondary structures that might interfere with assembly.

The light and heavy chain expression vectors are then co-transfected into the COS-PrP tet-inducible knock-out line by electroporation. Equal amounts of each plasmid DNA (10 μg) are added to 0.8 ml of cells suspended in PBS at $1 \times 10^7$ ml$^{-1}$. A pulse is delivered at 1.9 kV, 25 μF capacitance using a Gene Pulsar™ apparatus (BioRad). After a 10 minute recovery period at room temperature, the electroporated cells are added to 20 ml DMEM containing 10% gamma globulin-free fetal calf serum (GIBCO™). After a 2 hour incubation, the medium is collected, centrifuged to remove cellular debris, and purified.

The instant invention is shown and described herein in what is considered to be the most practical, and preferred embodiments. It is recognized, however, that departures may be made therefrom, which are within the scope of the invention, and that obvious modifications will occur to one skilled in the art upon reading this disclosure.

---

---

What is claimed is:

1. A method for producing a protein free from infectious prion contamination, comprising:
   a) ablating an endogenous PrP gene in a mammalian somatic host cells;
   b) operatively inserting a DNA sequence into said host cells which sequence encodes a protein; and
   c) isolating the protein from said host cells;
   wherein the isolated protein is an a composition which is characterized by an inability to transmit a prion-mediated pathology to a subject of the same species as the host cells.

2. The method of claim 1, wherein the protein is a human protein.

3. The method of claim 1, wherein both alleles of the endogenous PrP gene are ablated.

4. A method for producing therapeutic protein composition free from infectious prion contamination, comprising:
   a) ablating an endogenous PrP gene in a host mammalian cell;

b) introducing exogenous PrP sequences from a species genetically diverse from said host cell into said host cell;
c) expressing said exogenous PrP sequences;
d) operatively inserting a DNA sequence into said host cell which sequence encodes a protein; and
e) isolating a composition comprising the protein from said host cell;
wherein the expression of the exogenous PrP sequences allows necessary expression of PrP and wherein the isolated composition cannot transmit a prion-mediated pathology to a subject of the same species as the host cell.

5. The method of claim 4, wherein the exogenous PrP gene is operatively fused to an inducible promoter.

6. The method of claim 5, wherein the protein is human.

7. The method of claim 5, wherein both alleles of the endogenous PrP gene are ablated.

8. A method for producing a therapeutic protein composition free from infectious prion contamination, comprising:

a) ablating the endogenous PrP gene in a somatic host cell;
b) introducing exogenous PrP sequences from a genetically similar species, said exogenous sequences operably linked to an inducible promoter;
c) suppressing expression of the exogenous PrP sequences;
d) producing a therapeutic composition comprising a protein in said host cell; and
e) isolating the therapeutic composition from said host cell;
wherein the isolated therapeutic protein composition produced during suppression of PrP expression cannot transmit a prion-mediated pathology to a subject of the same species as the host cell.

9. The method of claim 8, wherein the protein is human.

10. The method of claim 8 wherein both alleles of the endogenous PrP gene are ablated.

* * * * *

UNITED STATES PATENT AND TRADEMARK OFFICE
CERTIFICATE OF CORRECTION

PATENT NO. : 7,163,806 B2
APPLICATION NO. : 10/773795
DATED : January 16, 2007
INVENTOR(S) : Stanley B. Prusiner et al.

It is certified that error appears in the above-identified patent and that said Letters Patent is hereby corrected as shown below:

In col. 20, claim 1, line 55, please delete "an" and insert therefore --in--;

In col. 21, claim 5, line 15, please delete "gene is" and insert therefore --sequences are--;

In col. 21, claim 6, line 16, please delete "5" and insert therefore --4--; and

In col. 21, claim 7, line 17, please delete "5" and insert therefore --4--.

Signed and Sealed this

Fifth Day of June, 2007

JON W. DUDAS
*Director of the United States Patent and Trademark Office*